United States Patent [19]
Gauthier-Lafaye et al.

[11] 4,431,835
[45] Feb. 14, 1984

[54] HYDROCARBONYLATION/CARBONYLATION OF ALKYL CARBOXYLATES

[75] Inventors: Jean Gauthier-Lafaye, Lyons; Robert Perron, Charly, both of France

[73] Assignee: Rhone-Poulenc Industries, Paris, France

[21] Appl. No.: 280,218

[22] Filed: Jul. 6, 1981

[30] Foreign Application Priority Data

Aug. 7, 1980 [FR] France ............................ 80 17704

[51] Int. Cl.³ .................. C07C 67/36; C07C 51/12; C07C 45/49; C07C 29/36
[52] U.S. Cl. ......................... 560/105; 260/409; 260/410.5; 260/410.9 R; 260/413; 560/1; 560/103; 560/106; 560/122; 560/123; 560/124; 560/232; 560/254; 560/265; 562/400; 562/406; 562/493; 562/496; 562/504; 562/505; 562/506; 562/517; 562/519; 562/606; 562/607; 568/428; 568/484; 568/715; 568/814; 568/876; 568/885

[58] Field of Search ............... 560/254, 232, 265, 105, 560/106, 103, 122–124, 1, 114; 260/410.9 R, 413, 409, 410.5; 562/406, 400, 517, 519, 606, 607, 493, 496–497, 504–506; 568/484, 885, 876, 428, 814, 715, 909

[56] References Cited

U.S. PATENT DOCUMENTS 4,133,966  1/1979  Pretzer et al. ...................... 560/265
4,189,441  2/1980  Braca et al. ........................... 56/265
4,239,924 12/1980  Pretzer et al. ...................... 560/265

Primary Examiner—Vivian Garner
Attorney, Agent, or Firm—Burns, Doane, Swecker & Mathis

[57] ABSTRACT

Alkyl carboxylates are hydrocarbonylated and/or carbonylated with carbon monoxide and hydrogen, in an aqueous medium, and in the presence of a catalytically effective amount of a catalyst system comprising (i) ruthenium, (ii) cobalt, (iii) at least one iodine-containing promoter, and (iv) chromium. The subject hydrocarbonylation/carbonylation is admirably well suited, e.g., for the preparation of acetaldehyde, ethanol, ethyl acetate and acetic acid, especially from a methyl carboxylate.

24 Claims, No Drawings

HYDROCARBONYLATION/CARBONYLATION OF ALKYL CARBOXYLATES

BACKGROUND OF THE INVENTION

1. Field of the Invention

The present invention relates to the hydrocarbonylation and/or carbonylation of alkyl carboxylates, in particular methyl carboxylates and alkyl acetates, in the presence of water. The subject process is, moreover, conveniently represented by the following equation:

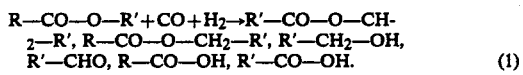

$$R-CO-O-R' + CO + H_2 \rightarrow R'-CO-O-CH_2-R', R-CO-O-CH_2-R', R'-CH_2-OH, R'-CHO, R-CO-OH, R'-CO-OH. \quad (1)$$

in which R represents a linear or branched chain alkyl radical having from 1 to 16 carbon atoms, a cycloalkyl radical having from 3 to 6 carbon atoms, a phenyl radical ($C_6H_5-$), a radical $C_6H_5-C_xH_{2x}-$ or a radical $C_xH_{2x+1}-C_6H_4-$, with x being an integer ranging from 1 to 6 ($1 \leq x \leq 6$), and R' represents a linear or branched chain alkyl radical having from 1 to 5 carbon atoms or a radical $C_6H_5-C_xH_{2x}-$, with x being as above defined, it also being possible for R and R' to be identical.

The process according to this invention is admirably suited to the preparation of one or more of the compounds acetaldehyde, acetic acid, ethanol and ethyl acetate, from methyl carboxylates, and especially from methyl acetate.

2. Description of the Prior Art

Certain authors (compare *Journal of the American Chemical Society*, 100:19, 1978, pages 6,238–6,239) have reported that it is possible to prepare, in particular, ethyl acetate by the hydrocarbonylation of methyl acetate in the simultaneous presence of ruthenium, an iodine-containing promoter and a proton donor (which is either the HI initially employed in the reaction, or formed in situ from $CH_3I$, or a carboxylic acid).

However, the industrial-scale development of a technique of this type, the value of which is not contested in principle, is markedly compromised by the low activity of the catalyst system used.

It has recently been proposed (compare French Patent Application No. 78/20,843) to carry out such reaction in the presence of a cobalt salt and iodine. However, the high pressures required for the catalyst system to develop an acceptable activity hardly make it possible to envisage industrial development of such a process.

Parallel to this, examination of the specialized literature reveals that numerous attempts to hydrocarbonylate methanol in order to selectively obtain either acetaldehyde or ethanol have not resulted in satisfactory solutions. A survey of the various techniques proposed for this purpose can be found, for example, in the introductory portion of U.S. Pat. No. 4,133,966.

It is clearly apparent from this analysis that it would be desirable to have available an efficient process which makes it possible, if appropriate, to prepare aldehydes, carboxylic acids, "homologous" alcohols and, more particularly, alkyl carboxylates from their lower homologs. The term "homologous alcohol" is to be understood as connoting the alcohol $R'-CH_2-OH$ shown in equation (1) above, which thus contains one carbon atom more than the alcohol ($R'-OH$) from which the starting ester is derived. A first category of alkyl carboxylates which can be obtained according to the present invention is represented by the formula $R-CO-O-CH_2-R'$ in equation (1) above. This type of ester contains one carbon atom more than the starting ester and can thus be considered as a "higher homolog" of the starting ester. To simplify the account below, the alkyl carboxylates of the formula $R'-CO-O-CH_2-R'$ shown in equation (1) above will also be referred to as "homologous esters".

SUMMARY OF THE INVENTION

Accordingly, and which is a major object of the present invention, a novel process is hereby provided which quite unexpectedly, enables hydrocarbonylation and/or carbonylation of alkyl carboxylates in an aqueous medium in order to obtain one or more of the compounds comprising the carboxylic acids, aldehydes, alcohols and homologous alkyl carboxylates, according to equation (1) above, in an extremely efficient manner, provided that the reaction is carried out in the presence of hydrogen, ruthenium, cobalt, at least one iodine-containing promoter and chromium (or a chromium compound).

DETAILED DESCRIPTION OF THE INVENTION

More particularly according to this invention, one of the essential constituents of the catalyst system consistent herewith is ruthenium. The precise form in which the ruthenium is employed in the reaction is not critical. Ruthenium carbonyls, such as $Ru_3(CO)_{12}$, $[Ru(CO)_3Br_2]_2$ and $Ru(CO)_4I_2$, and more generally any ruthenium compound which is capable of giving rise to, under the reaction conditions, the appearance of ruthenium carbonyls in situ, are particularly suitable for carrying out the subject process. Ruthenium metal in finely divided form, ruthenium tribromide, ruthenium triiodide, ruthenium carboxylates (in particular ruthenium acetate) and ruthenium acetylacetonate are exemplary in this respect.

The amount of ruthenium to be used is also not critical. As the proportion of ruthenium in the reaction medium has a beneficial influence on the reaction rate, it will be determined as a function of the rate which it will be judged suitable to attain.

In general, an amount ranging from 0.5 to 100 milligram atoms of ruthenium per liter of reaction medium (mg atoms/liter) affords satisfactory results. The reaction is preferably carried out with a proportion of ruthenium ranging from 1 to 50 mg atoms/liter of ruthenium.

The second essential, or critical constituent of the catalyst system is cobalt. Any source of cobalt which is capable of reacting with carbon monoxide in the reaction medium to provide cobalt carbonyl complexes can be used within the scope of the present process.

Examples of typical sources of cobalt are finely divided cobalt metal, inorganic salts, such as cobalt nitrate or carbonate, and organic salts, in particular carboxylates. Cobalt carbonyls or hydrocarbonyls can also be employed.

Cobalt formate, acetate and halides, and more particularly cobalt iodide, and dicobalt octacarbonyl are also exemplary of the cobalt derivatives suitable for carrying out the process according to the invention.

The precise amount of cobalt employed in the reaction too is not of fundamental importance. In general, the reaction is carried out with an amount of cobalt such that the atomic ratio Co/Ru ranges from 0.01 to 100

($0.01 \leq Co/Ru \leq 100$). This ratio preferably ranges from 0.1 to 10.

The presence of an iodine-containing promoter is also required for carrying out the process according to the present invention. Free or combined iodine can be used for this purpose.

A first category of iodine-containing promoters suitable for carrying out the subject process consists of alkyl or acyl iodides of the respective formulae R''—I and R''—CO—I, in which R'', which can be identical to or different from R', has the meaning given for R'. In this catetory, it is preferred to use alkyl iodides having a maximum of 4 carbon atoms and more particularly methyl or ethyl iodide.

A second category of iodine-containing promoters which can be used within the scope of the present process consists of ionic iodides, the cations of which are selected from among alkali metal cations, alkaline earth metal cations and the quaternary ammonium or phosphonium cations represented by the formulae I to III below:

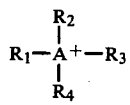
(I)

in which A represents a nitrogen or phosphorus atom, and $R_1$, $R_2$, $R_3$ and $R_4$, which can be identical or different, represent hydrogen or preferably organic radicals, the free valency of which is carried by a carbon atom, it optionally being possible for any two of these various radicals to together form a single divalent radical.

More specifically, $R_1$, $R_2$, $R_3$ and $R_4$ are advantageously linear or branched chain alkyl radicals, cycloalkyl radicals, aralkyl radicals (for example, benzyl) or monocyclic aryl radicals, which have at most 16 carbon atoms and which, if appropriate, can be substituted by 1 to 3 alkyl radicals having from 1 to 4 carbon atoms, it optionally being possible for two of the radicals $R_1$ to $R_4$ to together form a single divalent alkylene or alkenylene radical containing 3 to 6 carbon atoms and, if appropriate, 1 or 2 ethylenic double bonds, and it being possible for the said radical to bear 1 to 3 alkyl substituents having from 1 to 4 carbon atoms.

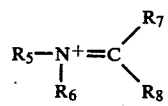
(II)

in which $R_5$, $R_6$, $R_7$ and $R_8$, which are identical or different, represent alkyl radicals having from 1 to 4 carbon atoms, it also being possible for one of the radicals $R_7$ or $R_8$ to represent hydrogen and it optionally being possible for $R_7$ and $R_8$ to together form a single divalent alkylene radical containing from 3 to 6 carbon atoms, for example, tetramethylene or hexamethylene; $R_6$ and $R_7$ or $R_8$ can together form a single divalent alkylene or alenkylene radical containing 4 carbon atoms and, if appropriate, 1 or 2 ethylenic double bonds, the nitrogen atom then being included in a heterocyclic ring to form, for example, a pyridinium cation.

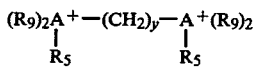
(III)

in which $R_5$ and $A^+$ have the meaning given above, $R_9$, which can be identical to $R_5$, represents an alkyl radical having from 1 to 4 carbon atoms or a phenyl radical and y is an integer ranging from 1 to 10 ($1 \leq y \leq 10$) and preferably from 1 to 6 ($1 \leq y \leq 6$). The following are exemplary of quaternary ammonium iodides suitable for carrying out the present process: tetramethylammonium, triethylmethylammonium, tributylmethylammonium, trimethyl-(n-propyl)-ammonium, tetraethylammonium, tetrabutylammonium, dodecyltrimethylammonium, benzyltrimethylammonium, benzyldimethylpropylammonium, benzyldimethyloctylammonium, dimethyldiphenylammonium, methyltriphenylammonium, N,N-dimethyl-trimethyleneammonium, N,N-diethyl-trimethyleneammonium, N,N-dimethyltetramethyleneammonium, N,N-diethyl-tetramethyleneammonium, N-methylpyridinium, N-ethylpyridinium and N-methylpicolinium iodides.

The following are exemplary quaternary phosphonium iodides also suitable for carrying out the present process: tetramethylphosphonium, ethyltrimethylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri-(isopropyl)phosphonium, methyl-tri-(n-propyl)-phosphonium, methyl-tri-(n-butyl)-phosphonium, methyl-tris-(2-methylpropyl)-phosphonium, methyltricyclohexylphosphonium, methyltriphenylphosphonium, methyltribenzylphosphonium, methyl-tris-(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri-(n-propyl)-phosphonium, triethylpentylphosphonium, ethyltriphenylphosphonium, n-butyl-tri-(n-propyl)-phosphonium, butyltriphenylphosphonium, benzyltriphenylphosphonium, ($\beta$-phenylethyl)-dimethylphenylphosphonium, tetraphenylphosphonium and triphenyl-(4-methylphenyl)-phosphonium iodides.

The precise nature of the quaternary ammonium or phosphonium cation is not of fundamental importance within the scope of the present process. The choice from among these compounds is governed more by considerations of a practical nature, such as solubility in the reaction medium, the availability and the convenience of use.

In this respect, the quaternary ammonium or phosphonium iodides represented either by the formula (I) in which any one of the radicals $R_1$ to $R_4$ is selected from among linear alkyl radicals having from 1 to 4 carbon atoms, or by the formulae (II) or (III) in which $R_5$ or $R_6$ is also an alkyl radical having from 1 to 4 carbon atoms, are particularly suitable.

Moreover, the preferred ammonium iodides are those in which the cations correspond to the formula (I) in which all the radicals $R_1$ to $R_4$ are selected from among linear alkyl radicals having from 1 to 4 carbon atoms, and in which at least three of same are identical.

Likewise, the preferred quaternary phosphonium iodides are those in which the cations correspond to the formula (I) in which any one of the radicals $R_1$ to $R_4$ represents a linear alkyl radical having from 1 to 4 carbon atoms, the other three radicals being identical and selected from among phenyl, tolyl or xylyl radicals.

The alkali metal iodides, in particular lithium, potassium and sodium iodides, constitute a preferred class of ionic iodides within the scope of the present invention. The quaternary phosphonium iodides, and more particularly those in which the cations correspond to the formula (I) above, in which one of the radicals $R_1$ to $R_4$ is an alkyl radical having from 1 to 4 carbon atoms, the other three radicals being identical and selected from among phenyl, tolyl or xylyl radicals, constitute another preferred class of ionic iodides which are particularly effective for carrying out the present invention.

Of course, hydriodic acid can also be used as the iodine-containing promoter; it is also possible to employ iodine-containing compounds such as $CoI_2$, $CrI_2$, $CrI_3(9H_2O)$, $RuI_3$ and $Ru(CO)_4I_2$, by themselves or, preferably, mixed with one or more iodine-containing promoters belonging to one or another of the aforenoted categories.

In general, the amount of iodine-containing promoter is such that the atomic ratio I/Ru is equal to at least 0.01; it serves no purpose to exceed a value of 2,000 for this ratio. This ratio advantageously ranges from 0.05 to 500.

According to a preferred embodiment of the subject process, an alkyl or acyl iodide (a member of the first category of iodine-containing promoters described above) is used simultaneously with an ionic iodide belonging to the second category of iodine-containing promoters mentioned above.

It too has been found that good results are obtained if an alkyl iodide (R"—I) is used simultaneously with an alkali metal iodide.

The simultaneous use of methyl iodide and an alkali metal iodide is particularly advantageous within the scope of the present process.

Another essential characteristic of the present invention is the use of chromium or a chromium compound. Although finely divided chromium metal and chromium hexacarbonyl can be used, it is preferred to use chromium salts in which the chromium is in an oxidation state (p) of more than zero (p>0), and which have the general formula $Cr_n{}^{p+}X_q{}^{m-}$, in which q denotes the ratio (nxp)/m, m is equal to 1 or 2, p=2, 3, 4 or 6, n being equal to 1 or 2 and being selected as a function of the respective values of m and p such that q is an integer, and $X^{m-}$ is an anion selected from the group comprising $OH^-$, $Cl^-$, $Br^-$, $I^-$, $O^=$, $PO_4^\equiv$, $CH_3COCH=C(CH_3)O^-$, $HCOO^-$, $C_2O_4^=$, $R^{10}$—$COO^-$, $R^{10}$—$O^-$, $NO_3^-$ and $CO_3^=$, $R^{10}$ having the meaning given for R and it being possible for $R^{10}$ and R to be identical or different; the chromium salts can be in hydrated form.

The precise nature of the anion $X^{m-}$ would not appear to be a fundamental parameter of the process according to this invention. The following are exemplary of chromium salts suitable for carrying out the present process: $Cr(OH)_3$, $CrCl_2$, $CrCl_3.6H_2O$, $CrI_2$, $CrBr_2$, $CrI_3.9H_2O$, $CrBr_3.6H_2O$, $CrO_3$, $Cr_2O_3$, $CrPO_4.6H_2O$, $Cr(OCOCH_3)_3.H_2O$, $Cr(NO_3)_3$, $CrCO_3$, $Cr(OCOCH_3)_2$, $Cr(OH)(HCO_2)_2$, $Cr[CH_3COCH=C(CH_3)O^-]_3$ and $CrC_2O_4.H_2O$.

According to a preferred embodiment of the invention, a chromium salt in which the chromium is in oxidation state 3 (p=3) is used. Chromium carboxylates, and more particularly acetates, are convenient to use and in this respect are recommended for carrying out the present invention.

The amount of chromium (or chromium compound) employed in the reaction is generally such that the atomic ratio Cr/Ru ranges from 0.5 to 500 ($0.5 \leq Cr/Ru \leq 500$). This ratio preferably ranges from 1 to 200.

According to the present invention, a mixture containing carbon monoxide and hydrogen is thus reacted with an alkyl carboxylate in the presence of water and the catalyst system defined above. In general, the water represents at least 1% by volume of the initial reaction medium and can be as high as 25% of the said volume. The reaction is advantageously carried out in the liquid phase under a pressure in excess of atmospheric. In general, it is carried out under a total pressure of at least 50 bars; a pressure of as much as 1,000 bars serves no purpose. To carry out the invention satisfactorily, a total pressure of 80 to 350 bars is recommended. The molar ratio of the carbon monoxide to the hydrogen can vary over wide limits.

If it is desired to assist the carbonylation of the starting material (the production of the carboxylic acid R'—CO—OH), the reaction is carried out with a mixture comprising a preponderant proportion of carbon monoxide and a small proportion of hydrogen; in general, a molar ratio $CO/H_2$ of more than 5 leads to satisfactory results in this case.

If it is desired to assist the hydrocarbonylation of the starting material (the production of R'—CHO, R'—CH$_2$OH, R—CO—O—CH$_2$—R' and R'—CO—O—CH$_2$—R'), the reaction is carried out with a mixture containing carbon monoxide and hydrogen in a molar ratio $CO/H_2$ ranging from 1/10 to 10/1 and preferably ranging from 1/5 to 5/1.

In all cases, substantially pure carbon monoxide and hydrogen, as available commercially, are employed. However, the presence of impurities, such as, for example, carbon dioxide, oxygen, methane and nitrogen, is not detrimental.

The reaction temperature is generally above 120° C. However, it serves no purpose to exceed a temperature of 300° C. Good results are obtained within the temperature range from 160° to 250° C.

As indicated in equation (1), the starting material is an alkyl carboxylate of the formula R—CO—O—R', in which R represents a linear or branched chain alkyl radical having from 1 to 16 carbon atoms, a cycloalkyl radical having from 3 to 6 carbon atoms, a phenyl radical ($C_6H_5$—), a radical $C_6H_5$—$C_xH_{2x}$— or a radical $C_xH_{2x+1}$—$C_6H_4$—, with x being an integer ranging from 1 to 6 ($1 \leq x \leq 6$), and R' represents a linear or branched chain alkyl radical having from 1 to 5 carbon atoms, it furthermore being possible for R and R' to be identical. R' is preferably a methyl radical. R is advantageously an alkyl radical having at most 4 carbon atoms or a radical $C_6H_5$—$CH_2$—. Alkyl acetates and benzoates, and more particularly methyl acetate and benzoate, are particularly suitable starting materials within the scope of the present invention.

Of course, the alkyl carboxylate (starting material) can be formed in situ from the corresponding carboxylic acid and alcohol of the formulae RCOOH and R'OH respectively.

It has also been determined that good results are obtained if the reaction medium also initially contains a carboxylic acid of the formula R'''COOH, in which R''' has the meaning given for R, it being possible for R''' and R to be identical or different. The initial reaction medium can contain up to 90% by volume of carboxylic acid (R'''COOH).

According to another preferred embodiment of the present process, the initial reaction medium contains from 1 to 20% by volume of water and from 5 to 50% by volume of carboxylic acid.

If the initial reaction medium contains a carboxylic acid (R''' COOH) which is different from the acid RCOOH from which the starting alkyl carboxylate is derived, the presence, among the reaction products, of the ester of the formula: R''' COOCH$_2$R', in which R' has the above meaning, is noted in certain instances.

If it is desired to carry out the reaction initially in the presence of a carboxylic acid (R''' COOH), acetic, propionic, butyric, benzoic or toluic acid is preferably used.

As indicated above, the present process has a particularly advantageous application in the preparation of one or more compounds selected from among acetaldehyde, acetic acid, ethanol and ethyl acetate, from methyl carboxylates and especially from methyl acetate.

As far as it is possible to determine, and without implying any limitation, the subject process which leads to the formation of the main products referred to above, can be directed towards the preferential production of one or other of the classes of products in question.

Thus, a reduction in the reaction temperature and/or in the proportion of hydrogen in the CO/H$_2$ mixture is capable of assisting the production of acetic acid. (Of course, in the case where the starting material is methyl acetate, some of the acetic acid formed originates from the hydrolysis reaction of the starting material.) On the other hand, an increase in the reaction temperature and/or in the proportion of hydrogen in the CO/H$_2$ mixture and, if appropriate, the presence of an increased proportion of ruthenium in the reaction medium seem to direct the reaction towards the preferential formation of ethyl acetate or ethanol.

An increase in the temperature and/or in the proportion of hydrogen in the CO/H$_2$ mixture, coupled with a reduction in the reaction time, would tend to assist the production of acetaldehyde.

Thus, it is possible to obtain free acetaldehyde, namely, acetaldehyde which is not substantially converted to dimethylacetal, in contrast to that which occurs to a more or less marked extent when attempting to obtain this product starting from free methanol. Those skilled in the art will appreciate the fact that the recovery of the acetaldehyde from the reaction medium is facilitated, especially if the reaction is carried out in the presence of a heavy carboxylic acid, such as benzoic acid, and/or if a heavy methyl carboxylate (for example, methyl benzoate) is selected as the starting material.

Upon completion of the reaction, the products obtained can easily be separated, for example, by fractional distillation of the resulting mixture.

In order to further illustrate the present invention and the advantages thereof, the following specific examples are given, it being understood that same are intended only as illustrative and in nowise limitative.

In said examples which follow, the following technique was employed:

The alkyl carboxylate (starting material), the catalyst system, distilled water and, if appropriate, a carboxylic acid were introduced into a Z-8 CNDT 17-12 stainless steel autoclave (AFNOR Standard Specification) having a capacity of 250 ml. After closing the autoclave, a pressure of 140 bars (unless otherwise indicated) was established with the aid of a mixture of carbon monoxide and hydrogen in a fixed molar ratio, as indicated in each of the following examples.

Shaking by means of a reciprocating system was commenced and the autoclave was then heated to the selected temperature over the course of about 25 minutes.

The pressure in the autoclave then increased and was maintained substantially at the value indicated in each of the following examples by successively introducing additional amounts of the initial CO/H$_2$ mixture. When the reaction time fixed for each example, at the indicated temperature, was reached, the heating and shaking were terminated. The autoclave was then cooled and degassed. After dilution, the resulting reaction mixture was analyzed by gas chromatography.

The results obtained are indicated in mols of products (in principle: acetaldehyde, ethanol, ethyl acetate and acetic acid) obtained per hour and per liter of reaction medium. The notation M/hour×liter is used for each product.

The results relating to the acetic acid include neither the amount of acetic acid which may have been introduced initially, nor the amount which was formed by hydrolysis of the methyl acetate (starting material).

Also, for a given product, Y indicates the selectivity of this product, relative to all of the products listed immediately above.

The degree of conversion, referred to as DC in the following text, is defined as being the ratio of the total number of mols of products in the list given above to the number of mols of methyl acetate introduced, reduced by the number of mols (of this starting material) hydrolyzed. (That fraction of the starting material hydrolyzed during an experiment can be measured by determining the methanol present in the liquid product obtained upon completion of the experiment).

EXAMPLE 1

Using the autoclave and the procedure described above, an experiment was carried out on a charge consisting of:
 (i) 80 ml of methyl acetate (1,000 mmols);
 (ii) 20 ml of acetic acid (350 mmols);
 (iii) 3 ml of water (170 mmols);
 (iv) 0.22 mg atom of cobalt, in the form of cobalt acetate tetrahydrate;
 (v) 1.30 mg atoms of ruthenium, in the form of triruthenium dodecacarbonyl;
 (vi) 8.34 mg atoms of chromium, in the form of chromium acetate; and
 (vii) 30 mmols of sodium iodide.

After a reaction time of 20 minutes at 215° C., with the pressure in the autoclave being maintained at about 250 bars by periodically introducing additional amounts of a ½ CO/H$_2$ mixture, the formation of:
 (1) 1.14 M/hour×liter of acetaldehyde (Y=15%);
 (2) 1.64 M/hour×liter of ethanol (Y=22%);
 (3) 2.96 M/hour×liter of ethyl acetate (Y=40%); and
 (4) 1.64 M/hour×liter of acetic acid (Y=22%);
was determined (DC=24.9%).

EXAMPLE 2

Using the autoclave and the procedure described above, an experiment was carried out on a charge consisting of:
 (i) 77 ml of methyl acetate (964 mmols);
 (ii) 20 ml of acetic acid (350 mmols);

(iii) 3 ml of water (170 mmols);
(iv) 0.22 mg atom of cobalt, in the form of cobalt acetate tetrahydrate;
(v) 1.30 mg atoms of ruthenium, in the form of triruthenium dodecacarbonyl;
(vi) 17 mg of chromium, in the form of chromium acetate; and
(vii) 35 mmol of methyl iodide.

After a reaction time of 20 minutes at 215° C., with the pressure in the autoclave being maintained at about 250 bars by periodically introducing additional amounts of a 1/2CO/$H_2$ mixture, the formation of:
(1) 0.79 M/hour×liter of acetaldehyde (Y=11%);
(2) 1.05 M/hour×liter of ethanol (Y=15%);
(3) 2.23 M/hour×liter of ethyl acetate (Y=32%); and
(4) 2.89 M/hour×liter of acetic acid (Y=42%);
was determined (DC=23.7%).

EXAMPLE 3

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 0.22 mg atom of cobalt, in the form of cobalt iodide;
(v) 1.30 mg atoms of ruthenium, in the form of triruthenium dodecacarbonyl;
(vi) 8.34 mg atoms of chromium, in the form of chromium acetate; and
(vii) 30 mmols of sodium iodide.

After a reaction time of 20 minutes at 215° C., with the pressure in the autoclave being maintained at about 245 bars by periodically introducing additional amounts of a 1/2CO/$H_2$ mixture, the formation of:
(1) 1.09 M/hour×liter of acetaldehyde (Y=13%);
(2) 1.66 M/hour×liter of ethanol (Y=20%);
(3) 3.33 M/hour×liter of ethyl acetate (Y=40%); and
(4) 2.18 M/hour×liter of acetic acid (Y=26%);
was determined (DC=27.5%).

EXAMPLE 4

Using the autoclave and the procedure described above, an experiment was carried out on a charge consisting of:
(i) 80 ml of ethyl acetate (791 mmols);
(ii) 20 ml of acetic acid (350 mmols);
(iii) 3 ml of water (170 mmols);
(iv) 0.42 mg atom of cobalt, in the form of cobalt iodide;
(v) 2.15 mg atoms of ruthenium, in the form of triruthenium dodecacarbonyl;
(vi) 33.4 mg atoms of chromium, in the form of chromium acetate;
(vii) 7.34 mmols of methyl iodide; and
(viii) 15 mmols of sodium iodide.

After a reaction time of 85 minutes at 213° C., with the pressure in the autoclave being maintained at about 230 bars by periodically introducing additional amounts of a 1/2CO/$H_2$ mixture, 0.47 M/hour×liter of propanol was obtained.

EXAMPLE 5

Using the autoclave and the procedure described above, an experiment was carried out on a charge consisting of:
(i) 90 ml of methyl acetate (1,125 mmols);
(ii) 10 ml of acetic acid (175 mmols);
(iii) 3 ml of water (170 mmols);
(iv) 0.33 mg atom of cobalt, in the form of cobalt iodide;
(v) 1.32 mg atoms of ruthenium, in the form of triruthenium dodecacarbonyl;
(vi) 16.7 mg atoms of chromium, in the form of chromium acetate;
(vii) 3.52 mmols of methyl iodide; and
(viii) 12 mmols of methyltriphenylphosphonium iodide.

After a reaction time of 30 minutes at 214° C., with the pressure in the autoclave being maintained at about 260 bars by periodically introducing additional amounts of a 1/2CO/$H_2$ mixture, the formation of
(1) 2.02 M/hour×liter of acetaldehyde (Y=22%);
(2) 0.57 M/hour×liter of ethanol (Y=6%);
(3) 3.24 M/hour×liter of ethyl acetate (Y=35%); and
(4) 3.54 M/hour×liter of acetic acid (Y=38%);
was determined (DC=41.6%).

EXAMPLE 6

Using the autoclave and the procedure described above, an experiment was carried out on a charge consisting of:
(i) 100 ml of methyl acetate (1,250 mmols);
(ii) 3 ml of water (170 mmols);
(iii) 1.28 mg atoms of cobalt, in the form of cobalt iodide;
(iv) 0.64 mg atom of ruthenium, in the form of triruthenium dodecacarbonyl;
(v) 16.7 mg atoms of chromium, in the form of chromium acetate;
(vi) 4.5 mmols of methyl iodide; and
(vii) 15 mmols of tetraethylammonium iodide.

After a reaction time of 35 minutes at 204° C., with the pressure in the autoclave being maintained at about 260 bars by periodically introducing additional amounts of a 1/1CO/$H_2$ mixture, the following were otained:
(1) 1.56 M/hour×liter of acetaldehyde (Y=36%);
(2) 1.65 M/hour×liter of ethyl acetate (Y=38%); and
(3) 1.16 M/hour×liter of acetic acid (Y=27%).
No ethanol was detected. (DC=16.9%).

EXAMPLE 7

Using the autoclave and the procedure described above, an experiment was carried out on a charge consisting of:
(i) 50 ml of methyl acetate (626 mmols);
(ii) 50 ml of acetic acid (875 mmols);
(iii) 3 ml of water (170 mmols);
(iv) 1.28 mg atoms of cobalt, in the form of cobalt iodide;
(v) 0.64 mg atom of ruthenium, in the form of triruthenium dodecacarbonyl;
(vi) 16.7 mg atoms of chromium, in the form of chromium acetate;
(vii) 1 mmol of methyl iodide; and
(viii) 15 mmols of tetraethylammonium iodide.

After a reaction time of 35 minutes at 204° C. with the pressure in the autoclave being maintained at about 260 bars by periodically introducing additional amounts of a 1/1CO/H$_2$ mixture, the formation of:
(1) 2.01 M/hour×liter of acetaldehyde (Y=70%);
(2) 0.07 M/hour×liter of ethanol (Y=2.4%); and
(3) 0.80 M/hour×liter of ethyl acetate (Y=28%);
was determined (DC=26.8%).

EXAMPLE 8

Using the autoclave and the procedure described above, an experiment was carried out on a charge consisting of:
(i) 80 ml of methyl acetate (1,000 mmols);
(ii) 20 ml of acetic acid (350 mmols);
(iii) 6 ml of water (340 mmols);
(iv) 1.28 mg atoms of cobalt, in the form of cobalt iodide;
(v) 0.64 mg atom of ruthenium, in the form of triruthenium dodecacarbonyl;
(vi) 16.7 mg atoms of chromium, in the form of chromium acetate;
(vii) 4.56 mmols of methyl iodie; and
(viii) 15 mmols of tetraethylammonium iodide.

After a reaction time of 35 minutes at 204° C., with the pressure in the autoclave being maintained at about 260 bars by periodically introducing additional amounts of a 1/1CO/H$_2$ mixture, the formation of:
(1) 2.98 M/hour×liter of acetaldehyde (Y=62%);
(2) 0.09 M/hour×liter of ethanol (Y=1.9%);
(3) 0.46 M/hour×liter of ethyl acetate (Y=9.6%); and
(4) 1.25 M/hour×liter of acetic acid (Y=26%);
was determined (DC=27.9%).

EXAMPLE 9

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 1.28 mg atoms of cobalt, in the form of cobalt iodide;
(v) 0.64 mg atom of ruthenium, in the form of triruthenium dodecacarbonyl;
(vi) 16.7 mg atoms of chromium, in the form of chromium acetate;
(vii) 1 mmol of methyl iodide; and
(viii) 15 mmols of tetraethylammonium iodide.

A pressure of 70 bars was established with the aid of a 1/1CO/H$_2$ mixture. The shaking was commenced and the autoclave was heated to 204° C. The pressure in the autoclave was maintained at about 150 bars by periodically introducing additional amounts of the 1/1CO/H$_2$ mixture. After a reaction time of 35 minutes at the temperature indicated, the formation of:
(1) 1.33 M/hour×liter of acetaldehyde (Y=40%);
(2) 0.49 M/hour×liter of ethyl acetate (Y=15%); and
(3) 1.54 M/hour×liter of acetic acid (Y=46%);
was determined.
Virtually no ethanol was detected. (DC=19.5%).

EXAMPLE 10

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 1.28 mg atoms of cobalt, in the form of cobalt iodide;
(v) 0.64 mg atom of ruthenium, in the form of triruthenium dodecacarbonyl;
(vi) 16.7 mg atoms of chromium, in the form of chromium acetate;
(vii) 1 mmol of methyl iodide; and
(viii) 15 mmols of tetraethylammonium iodide.

A pressure of 105 bars was established with the aid of a 1/2CO/H$_2$ mixture. The autoclave was heated to 206° C.; the pressure in the autoclave was maintained at about 205 bars by periodically introducing additional amounts of the above-mentioned CO/H$_2$ mixture. After a reaction time of 35 minutes at the temperature indicated, the formation of:
(1) 1.95 M/hour×liter of acetaldehyde (Y=45%);
(2) 0.11 M/hour×liter of ethanol (Y=2.5%);
(3) 0.59 M/hour×liter of ethyl acetate (Y=14%); and
1.71 M/hour×liter of acetic acid (Y=39%);
was determined (DC=25.6%).

EXAMPLE 11

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 1.28 mg atoms of cobalt, in the form of cobalt iodide;
(v) 0.64 mg atom of ruthenium, in the form of triruthenium dodecacarbonyl;
(vi) 16.7 atoms of chromium, in the form of chromium acetate;
(vii) 1 mmol of methyl iodide; and
(viii) 15 mmols of tetraethylammonium iodide.

An initial pressure of 105 bars was established with the aid of a 2/1CO/H$_2$ mixture and the autoclave was heated to 204° C. The pressure in the autoclave was maintained at about 205 bars by periodically introducing additional amounts of the above-mentioned CO/H$_2$ mixture. After a reaction time of 35 minutes at the temperature indicated, the formation of:
(1) 2.07 M/hour×liter of acetaldehyde (Y=50%);
(2) 0.31 M/hour×liter of ethyl acetate (Y=7%); and
(3) 1.80 M/hour×liter of acetic acid (Y=43%);
was determined.
Virtually no ethanol is detected (DC=24.3%).

EXAMPLE 12

Using the autoclave and the procedure described above, and experiment was carried out on a charge consisting of:
(i) 80 ml of methyl acetate (1,000 mmols);
(ii) 20 ml of acetic acid (350 mmols);
(iii) 3 ml of water (170 mmols);
(iv) 1.28 mg atoms of cobalt, in the form of cobalt iodide;
(v) 0.64 mg atom of ruthenium, in the form of triruthenium dodecacarbonyl;
(vi) 16.7 mg atoms of chromium, in the form of chromium acetate;
(vii) 1 mmol of methyl iodide; and
(viii) 15 mmols of tetraethylammonium iodide.

After a reaction time of 35 minutes at 205° C., with the pressure in the autoclave being maintained at about 250 bars by periodically introducing additional amounts of a 1/1CO/H$_2$ mixture, the formation of:
(1) 2.30 M/hour×liter of acetaldehyde (Y=60%);
(2) 0.38 M/hour×liter of ethyl acetate (Y=10%); and
(3) 1.13 M/hour×liter of acetic acid (Y=30%);
was determined.

Virtually no ethanol was detected (DC=22.2%).

EXAMPLE 13

Using the autoclave and the procedure described above, an experiment was carried out on a charge consisting of:
(i) 90 ml of methyl acetate (1,125 mmols);
(ii) 10 ml of acetic acid (175 mmols);
(iii) 3 ml of water (170 mmols);
(iv) 1.32 mg atoms of cobalt, in the form of cobalt iodide;
(v) 0.64 mg atom of ruthenium, in the form of triruthenium dodecacarbonyl;
(vi) 33.4 mg atoms of chromium, in the form of chromium acetate;
(vii) 4.4 mmols of methyl iodide; and
(viii) 12 mmols of sodium iodide.

After a reaction time of 20 minutes at 203° C., with the pressure in the autoclave being maintained at about 240 bars by periodically introducing additional amounts of a 1/1CO/H$_2$ mixture, the formation of:
(1) 2.35 M/hour×liter of acetaldehyde (Y=85%);
(2) 0.16 M/hour×liter of ethanol (Y=6%); and
(3) 0.27 M/hour×liter of ethyl acetate (Y=10%);
was determined (DC=8.3%).

EXAMPLE 14

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 1.28 mg atoms of cobalt, in the form of cobalt iodide;
(v) 0.64 mg atom of ruthenium, in the form of triruthenium dodecacarbonyl;
(vi) 16.7 mg atoms of chromium, in the form of chromium acetate;
(vii) 1 mmol of methyl iodide; and
(viii) 12 mmols of sodium iodide.

After a reaction time of 35 minutes at 206° C., with the pressure in the autoclave being maintained at about 255 bars by periodically introducing additional amounts of a 1/1CO/H$_2$ mixture, the formation of:
(1) 2.49 M/hour×liter of acetaldehyde (Y=54%);
(2) 0.21 M/hour×liter of ethanol (Y=5%);
(3) 0.74 M/hour×liter of ethyl acetate (Y=16%); and
(4) 1.15 M/hour×liter of acetic acid (Y=25%);
was determined (DC=26.8%).

EXAMPLE 15

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 1.28 mg atoms of cobalt, in the form of cobalt iodide;
(v) 0.64 mg atom of ruthenium, in the form of triruthenium dodecacarbonyl;
(vi) 16.7 mg atoms of chromium, in the form of chromium acetate;
(vii) 4.5 mmols of methyl iodide; and
(viii) 15 mmols of tetraethylammonium iodide.

After a reaction time of 35 minutes at 205° C., with the pressure in the autoclave being maintained at about 250 bars by periodically introducing additional amounts of a 1/1CO/H$_2$ mixture, the formation of:
(1) 2.51 M/hour×liter of acetaldehyde (Y=72%);
(2) 0.44 M/hour×liter of ethyl acetate (Y=13%); and
(3) 0.56 M/hour×liter of acetic acid (Y=16%);
was determined.

Virtually no ethanol was detected (DC=20.6%).

EXAMPLE 16

(i) 80 ml of methyl acetate (1,000 mmols);
(ii) 20 ml of acetic acid (350 mmols);
(iii) 3 ml of water (170 mmols);
(iv) 1.28 mg atoms of cobalt, in the form of cobalt iodide;
(v) 0.64 mg atom of ruthenium, in the form of triruthenium dodecacarbonyl;
(vi) 16.7 mg atoms of chromium, in the form of chromium acetate;
(vii) 4.3 mmols of methyl iodide; and
(viii) 15 mmols of tetraethylammonium iodide.

After a reaction time of 35 minutes at 190° C., with the pressure in the autoclave being maintained at about 250 bars by periodically introducing additional amounts of a 1/1CO/H$_2$ mixture, the formation of:
(1) 2.65 M/hour×liter of acetaldehyde (Y=66%);
(2) 0.21 M/hour×liter of ethyl acetate (Y=5%); and
(3) 1.14 M/hour×liter of acetic acid (Y=29%);
was determined.

Virtually no ethanol was detected (DC=23.4%).

EXAMPLE 17

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 1.28 mg atoms of cobalt, in the form of cobalt iodide;
(v) 0.64 mg atom of ruthenium, in the form of triruthenium dodecacarbonyl;
(vi) 16.7 mg atoms of chromium, in the form of chromium acetate;
(vii) 1 mmol of methyl iodide; and
(viii) 15 mmols of tetraethylammonium iodide.

After a reaction time of 20 minutes at 203° C., with the pressure in the autoclave being maintained at about 250 bars by periodically introducing additional amounts of a 1/1CO/H$_2$ mixture, the formation of:
(1) 3.99 M/hour×liter of acetaldehyde (Y=65%);
(2) 0.16 M/hour×liter of ethanol (Y=2.6%);
(3) 0.38 M/hour×liter of ethyl acetate (Y=5%); and
(4) 1.58 M/hour×liter of acetic acid (Y=26%);
was determined (DC=20.4%).

EXAMPLE 18

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 0.34 mg atom of cobalt, in the form of cobalt iodide;
(v) 1.97 mg atoms of ruthenium, in the form of triruthenium dodecacarbonyl;
(vi) 33.4 mg atoms of chromium, in the form of chromium acetate;
(vii) 7.67 mmols of methyl iodide; and
(viii) 15 mmols of sodium iodide.

After a reaction time of 40 minutes at 215° C., with the pressure in the autoclave being maintained at about 240 bars by periodically introducing additional amounts of a 1/2CO/H$_2$ mixture, the formation of:
(1) 0.39 M/hour×liter of acetaldehyde (Y=7%);
(2) 0.99 M/hour×liter of ethanol (Y=17%);
(3) 4.13 M/hour×liter of ethyl acetate (Y=72%); and
(4) 0.26 M/hour×liter of acetic acid (Y=5%);
was determined (DC=38.5%).

EXAMPLES 19 TO 22

Using the autoclave and the procedure described above, a series of experiments was carried out on a charge containing:
(i) methyl acetate;
(ii) chromium, in the form of chromium acetate;
(iii) 20 ml of acetic acid (350 mmols);
(iv) 5 ml of water (280 mmols);
(v) 0.22 mg atom of cobalt, in the form of cobalt acetate tetrahydrate;
(vi) 1.31 mg atoms of ruthenium, in the form of triruthenium dodecacarbonyl; and
(vii) 17.5 mmols of methyl iodide.

All of these experiments were carried out at 214° C., with the pressure in the autoclave being maintained at about 250 bars by periodically introducing additional amounts of a 1/2CO/H$_2$ mixture. The reaction time was 20 minutes. The particular conditions and also the results obtained are reported in Table I below.

Control experiment (a) was carried out in the absence of chromium; the reaction time was 30 minutes.

TABLE I

| Example No. | Methyl acetate mmols | Methyl acetate ml | Chromium in mg atoms | Acetaldehyde M/hour × liter | Acetaldehyde Y (%) | Ethanol M/hour × liter | Ethanol Y (%) | Ethyl acetate M/hour × liter | Ethyl acetate Y (%) | Acetic acid M/hour × liter | Acetic acid Y (%) | DC in % |
|---|---|---|---|---|---|---|---|---|---|---|---|---|
| a | 977 | 78 | 0 | — | — | 0.26 | 17 | 0.65 | 42 | 0.62 | 41 | 7.7 |
| 19 | 939 | 75 | 10 | 1.69 | 18 | 0.96 | 10 | 3.74 | 41 | 2.81 | 31 | 33.3 |
| 20 | 939 | 75 | 25 | 1.63 | 15 | 0.94 | 9 | 4.20 | 39 | 4.02 | 37 | 40.2 |
| 21 | 914 | 73 | 40 | 1.00 | 10 | 0.90 | 9 | 4.10 | 39 | 4.45 | 43 | 40.4 |
| 22 | 877 | 70 | 60 | 0.99 | 10 | 1.08 | 11 | 4.19 | 42 | 3.69 | 37 | 39.4 |

EXAMPLES 23 to 30

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 0.22 mg atom of cobalt, in the form of dicobalt octacarbonyl;
(v) 1.32 mg atoms of ruthenium, in the form of triruthenium dodecacarbonyl;
(vi) 3.52 mmols of methyl iodide; and
(vii) 12 mmols of ionic iodide.

Control experiment (b) was carried out in the absence of chromium; in Example 23, chromium hexacarbonyl was introduced, and in the other examples, chromium acetate was introduced.

For all of these experiments, a 1/2CO/H$_2$ mixture was used. The particular conditions and also the results obtained are reported in Table II below, in which Pt denotes the total pressure and T the reaction temperature.

TABLE II

| Example No. | Chromium mg/atoms | (x) | Pt bars | T °C. | Time minutes | Acetaldehyde M/hour × liter | Acetaldehyde Y (%) | Ethanol M/hour × liter | Ethanol Y (%) | Ethyl acetate M/hour × liter | Ethyl acetate Y (%) | Acetic acid M/hour × liter | Acetic acid Y (%) | DC in % |
|---|---|---|---|---|---|---|---|---|---|---|---|---|---|---|
| b | 0 | Na | 260 | 216 | 75 | 0.18 | 9 | 0.32 | 16 | 1.45 | 72 | 0.06 | 3 | 25.1 |
| 23 | 16.7 | Na | 260 | 210 | 40 | 0.34 | 12 | 0.41 | 15 | 1.63 | 60 | 0.35 | 13 | 18.2 |
| 24 | 8.3 | Na | 260 | 216 | 50 | 0.38 | 9 | 0.76 | 18 | 2.37 | 57 | 0.64 | 15 | 34.5 |
| 25 | 16.7 | Na | 240 | 215 | 40 | 0.55 | 12 | 0.73 | 15 | 3.47 | 73 | — | — | 31.6 |
| 26 | 33.3 | Na | 260 | 218 | 30 | 0.77 | 10 | 0.80 | 10 | 4.09 | 51 | 2.41 | 30 | 40.3 |
| 27 | 16.7 | A | 250 | 216 | 30 | 1.02 | 12 | 0.91 | 11 | 4.22 | 51 | 2.16 | 26 | 41.6 |
| 28 | 16.7 | B | 250 | 216 | 35 | 1.15 | 18 | 0.62 | 10 | 2.63 | 42 | 1.82 | 29 | 36.2 |
| 29 | 16.7 | Li | 250 | 215 | 35 | 0.80 | 12 | 0.89 | 13 | 3.70 | 56 | 1.23 | 19 | 38.7 |
| 30 | 16.7 | Cs | 250 | 215 | 60 | 0.43 | 19 | 0.36 | 16 | 1.40 | 62 | 0.08 | 3 | 22.7 |

N.B.
(x): nature of the cation of the ionic iodide.
A: denotes the cation [CH$_3$(C$_6$H$_5$)$_3$P]

B: denotes the cation 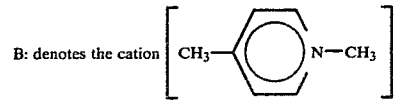

EXAMPLES 31 to 35

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 0.22 mg atom of cobalt, in the form of cobalt iodide;
(v) 1.32 mg atoms of ruthenium, in the form of triruthenium dodecacarbonyl;
(vi) 16.7 mg atoms of chromium, in the form of chromium acetate;
(vii) 3.52 mmols of methyl iodide; and
(viii) 15 mmols of tetraethylammonium iodide.

The reaction temperature was 215° C. (unless otherwise indicated); the pressure in the autoclave was maintained at about 255 bars by periodically introducing additional amounts of a 1/1CO/H$_2$ mixture. The reaction time and also the results obtained for each experiment are reported in Table III below.

TABLE III

| Example No. | Time minutes | Acetaldehyde M/hour × liter | Y (%) | Ethanol M/hour × liter | Y (%) | Ethyl acetate M/hour × liter | Y (%) | Acetic acid M/hour × liter | Y (%) | DC % |
|---|---|---|---|---|---|---|---|---|---|---|
| 31 | 10 | 6.82 | 61 | 1.04 | 9 | 1.84 | 17 | 1.45 | 13 | 18.6 |
| 32 | 20 | 3.78 | 46 | 0.65 | 8 | 1.57 | 19 | 2.13 | 26 | 27.1 |
| 33 | 35 | 1.33 | 22 | 0.49 | 8 | 2.64 | 43 | 1.66 | 27 | 35.6 |
| 34x | 35 | 2.18 | 35 | 0.30 | 5 | 0.81 | 13 | 2.86 | 47 | 27.4 |
| 35 | 50 | 1.2 | 27 | 0.30 | 7 | 1.51 | 34 | 1.42 | 32 | 36.9 | x: this experiment was carried out at 205° C.

EXAMPLES 36 to 38

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 0.64 mg atom of cobalt, in the form of cobalt iodide;
(v) triruthenium dodecacarbonyl, in the amount shown in Table IV below;
(vi) 16.7 mg atoms of chromium, in the form of chromium acetate;
(vii) 2.27 mmols of methyl iodide; and
(viii) 15 mmols of tetraethylammonium iodide.

The results obtained after a reaction time of 35 minutes at 205° C., with the pressure in the autoclave being maintained at about 250 bars by periodically introducing additional amounts of a 1/1CO/H$_2$ mixture, are also reported in Table IV below.

In this series of experiments, virtually no ethanol was detected.

EXAMPLE 39

Using the autoclave and the procedure described above, an experiment was carried out on a charge consisting of:
(i) 80 ml of methyl benzoate (635 mmols);
(ii) 20 ml of acetic acid (350 mmols);
(iii) 3 ml of water (170 mmols);
(iv) 0.4 mg atom of cobalt, in the form of cobalt iodide;
(v) 2.35 mg atoms of ruthenium, in the form of triruthenium dodecacarbonyl;
(vi) 33.4 mg atoms of chromium, in the form of chromium acetate;
(vii) 9.72 mmols of methyl iodide; and
(viii) 15 mmols of sodium iodide.

After a reaction time of 30 minutes at 214° C., with the pressure in the autoclave being maintained at about 250 bars by periodically introducing additional amounts of a 1/2CO/H$_2$ mixture, the formation of:
(1) 0.27 M/hour × liter of acetaldehyde;
(2) 1.78 M/hour × liter of ethanol;
(3) 2.52 M/hour × liter of ethyl acetate; and
(4) 0.57 M/hour × liter of ethyl benzoate;
was determined.

EXAMPLE 40

Using the autoclave and the procedure described above, an experiment was carried out on a charge consisting of:
(i) 80 ml of methyl benzoate (635 mmols);
(ii) 21.4 g of benzoic acid (175 mmols);
(iii) 3 ml of water (170 mmols);
(iv) 0.40 mg atom of cobalt, in the form of cobalt iodide;
(v) 2.34 mg atoms of ruthenium, in the form of triruthenium dodecacarbonyl;
(vi) 33.4 mg atoms of chromium, in the form of chromium acetate;
(vii) 9.5 mmols of methyl iodide; and
(viii) 15 mmols of sodium iodide.

After a reaction time of 30 minutes at 215° C., with the pressure in the autoclave being maintained at about 250 bars by periodically introducing additional amounts of a 1/2CO/H$_2$ mixture, the formation of:
(1) 2.48 M/hour × liter of ethanol;
(2) 0.86 M/hour × liter of ethyl acetate;
(3) 0.83 M/hour × liter of acetic acid; and

TABLE IV

| Example No. | Ru mg atoms | Acetaldehyde M/hour × liter | Y (%) | Ethyl acetate M/hour × liter | Y (%) | Acetic acid M/hour × liter | Y (%) | DC % |
|---|---|---|---|---|---|---|---|---|
| 36 | 0.17 | 2.04 | 68 | 0.29 | 10 | 0.69 | 23 | 17.6 |
| 37 | 0.33 | 2.30 | 60 | 0.41 | 11 | 1.12 | 29 | 22.3 |
| 38 | 0.65 | 2.94 | 77 | 0.46 | 12 | 0.39 | 10 | 22.2 |

(4) 1.46 M/hour×liter of ethyl benzoate; was determined.

EXAMPLE 41

Using the autoclave and the procedure described above, an experiment was carried out on a charge consisting of:
(i) 80 ml of methyl acetate (1,000 mmols);
(ii) 21.4 g benzoic acid (175 mmols);
(iii) 3 ml of water (170 mmols);
(iv) 0.22 mg atom of cobalt, in the form of cobalt iodide;
(v) 1.30 mg atoms of ruthenium, in the form of triruthenium dodecacarbonyl;
(vi) 16.7 mg atoms of chromium, in the form of chromium acetate;
(vii) 3.51 mmols of methyl iodide; and
(viii) 11.9 mmols of caesium iodide.

After a reaction time of 60 minutes at 214° C., with the pressure in the autoclave being maintained at about 260 bars by periodically introducing additional amounts of a 1/2CO/$H_2$ mixture, the formation of:
(1) 0.13 M/hour×liter of acetaldehyde;
(2) 0.73 M/hour×liter of ethanol;
(3) 2.22 M/hour×liter of ethyl acetate; and
(4) 0.02 M/hour×liter of ethyl benzoate;
was determined.

EXAMPLE 42

Using the autoclave and the procedure described above, an experiment was carried out on a charge consisting of:
(i) 73 ml of methyl acetate (914 mmols);
(ii) 20 ml of acetic acid (350 mmols);
(iii) 5 ml of water (280 mmols);
(iv) 0.22 mg atom of cobalt, in the form of cobalt acetate tetrahydrate;
(v) 0.65 mg atom of ruthenium, in the form of triruthenium dodecacarbonyl;
(vi) 40 mg atoms of chromium, in the form of chromium acetate; and
(vii) 17.9 mmols of methyl iodide.

After a reaction time of 20 minutes at 214° C., with the pressure in the autoclave being maintained at about 250 bars by periodically introducing additional amounts of a 13/1CO/$H_2$ mixture, the formation of:
(1) 0.98 M/hour×liter of acetaldehyde (Y=32%);
(2) 0.031 M/hour×liter of ethanol (Y=1%);
(3) 0.052 M/hour×liter of ethyl acetate (Y=1.7%); and
(4) 2.02 M/hour×liter of acetic acid (Y=65%);
was determined (DC=11.3%).

EXAMPLE 43

Using the autoclave and the procedure described above, an experiment was carried out on a charge consisting of:
(i) 80 ml of methyl acetate (1,000 mmols);
(ii) 20 ml of acetic acid (350 mmols);
(iii) 0.6 ml of water (33 mmols);
(iv) 0.22 mg atom of cobalt, in the form of cobalt acetate tetrahydrate;
(v) 1.31 mg atoms of ruthenium, in the form of triruthenium dodecacarbonyl; and
(vi) 15 mg atoms of chromium, in the form of $CrI_3.9-H_2O$.

After a reaction time of 20 minutes at 214° C., with the pressure in the autoclave being maintained at about 250 bars by periodically introducing additional amounts of a 2/1CO/$H_2$ mixture, the formation of:
(1) 1.49 M/hour×liter of acetaldehyde (Y=18%);
(2) 0.65 M/hour×liter of ethanol (Y=8%);
(3) 3.55 M/hour×liter of ethyl acetate (Y=44%); and
(4) 2.4 M/hour×liter of acetic acid (Y=30%);
was determined (DC=29%).

EXAMPLE 44

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 0.22 mg atom of cobalt, in the form of cobalt acetate tetrahydrate;
(v) 1.31 mg atoms of ruthenium, in the form of triruthenium dodecacarbonyl;
(vi) 15 mg atoms of chromium, in the form of $CrI_2$; and
(vii) 30 mmols of sodium iodide.

After a reaction time of 20 minutes at 214° C., with the pressure in the autoclave being maintained at about 250 bars by periodically introducing additional amounts of a 2/1CO/$H_2$ mixture, the formation of:
(1) 1.00 M/hour×liter of acetaldehyde (Y=15%);
(2) 0.99 M/hour×liter of ethanol (Y=15%);
(3) 2.63 M/hour×liter of ethyl acetate (Y=41%); and
(4) 1.81 M/hour×liter of acetic acid (Y=28%);
was determined (DC=21.4%).

EXAMPLE 45

Using the autoclave and the procedure described above, an experiment was carried out on a charge consisting of:
(i) 80 ml of methyl acetate (1,000 mmols);
(ii) 20 ml of acetic acid (350 mmols);
(iii) 3 ml of water (170 mmols);
(iv) 0.22 mg atom of cobalt, in the form of cobalt acetate tetrahydrate;
(v) 1.31 mg atoms of ruthenium, in the form of triruthenium dodecacarbonyl;
(vi) 15 mg atoms of chromium, in the form of chromium hexacarbonyl;
(vii) 30 mg atoms of iodine; and
(viii) 30 mmols of sodium iodide.

After a reaction time of 20 minutes at 214° C., with the pressure in the autoclave being maintained at about 250 bars by periodically introducing additional amounts of a 2/1CO/$H_2$ mixture, the formation of:
(1) 1.10 M/hour×liter of acetaldehyde (Y=21%);
(2) 0.90 M/hour×liter of ethanol (Y=17%);
(3) 1.73 M/hour×liter of ethyl acetate (Y=34%); and
(4) 1.43 M/hour×liter of acetic acid (Y=28%);
was determined (DC=17.5%).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the hydrocarbonylation and/or carbonylation of an alkyl carboxylate having the formula R-CO-O-R', in which R represents a linear or branched chain alkyl radical having from 1 to 16 carbon atoms, a cycloalkyl radical having from 3 to 6 carbon atoms, a phenyl radical, a radical

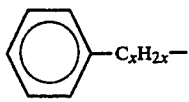

or a radical

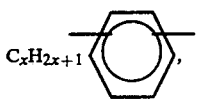

with x being an integer ranging from 1 to 6, and R' represents a linear or branched chain alkyl radical having 1 to 5 carbon atoms or a radical

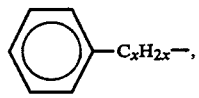

with x being as above defined and further in which R and R' may be the same or different, comprising reacting the alkyl carboxylate with carbon monoxide and hydrogen, in an aqueous medium, in the liquid phase and in the presence of a catalytically effective amount of (i) ruthenium, (ii) cobalt, (iii) at least one iodine-containing promoter, and (iv) chromium.

2. The process as defined by claim 1, wherein R' is methyl.

3. The process as defined by claims 1 or 2, wherein R is an alkyl radical having up to 4 carbon atoms, or benzyl.

4. The process as defined by claim 1, the reaction medium comprising from 0.5 to 100 milligram atoms of ruthenium per liter thereof.

5. The process as defined by claim 4, the reaction medium comprising from 1 to 50 milligram atoms of ruthenium per liter thereof.

6. The process as defined by claim 4, the atomic ratio Co/Ru in said catalyst system ranging from 0.01 to 100.

7. The process as defined by claim 6, said atomic ratio Co/Ru ranging from 0.1 to 10.

8. The process as defined by claim 6, said iodine-containing promoter (iii) comprising an ionic iodide, the cation of which being an alkali or alkaline earth metal cation, a quaternary ammonium cation, or a phosphonium cation.

9. The process as defined by claim 6, said iodine-containing promoter (iii) being an alkyl or acyl iodide.

10. The process as defined by claims 8 or 9, the atomic ratio I/Ru in said catalyst system ranging from 0.01 to 2,000.

11. The process as defined by claim 10, said atomic ratio I/Ru ranging from 0.05 to 500.

12. The process as defined by claim 10, the atomic ratio Cr/Ru in said catalyst system ranging from 0.5 to 500.

13. The process as defined by claim 12, said atomic ratio Cr/Ru ranging from 1 to 200.

14. The process as defined by claim 8, said iodine-containing promoter (iii) comprising the ionic iodide together with an alkyl iodide.

15. The process as defined by claims 9 or 14, the alkyl iodide being methyl iodide.

16. The process as defined by claim 1, the chromium component (iv) of said catalyst system comprising a chromium salt in which the chromium is in an oxidation state (p) of more than zero ($p>0$), and which has the general formula $Cr_n{}^{p+}X_q{}^{m-}$, in which q denotes the ratio $(n \times p)/m$, m is equal to 1 or 2, $p=2, 3, 4$ or 6, n being equal to 1 or 2 and being selected as a function of the respective values of m and p such that q is an integer, and $X^{m-}$ is an anion selected from the group comprising $OH^-$, $Cl^-$, $Br^-$, $I^-$, $O^=$, $CH_3COCH{=}C(CH_3)O^-$, $HCOO^-$, $C_2O_4{}^=$, $R^{10}\text{-}COO^-$, $R^{10}\text{-}O^-$, $NO_3{}^-$ and $CO_3{}^=$, $R^{10}$ is defined as was R and further in which $R^{10}$ and R may be identical or different.

17. The process as defined by claim 16, said chromium salt being in an oxidation state (p) of 3.

18. The process as defined by claims 16 or 17, said chromium salt being a chromium carboxylate.

19. The process as defined by claim 18, said chromium salt being chromium acetate.

20. The process as defined by claim 1, the initial reaction medium comprising from 1 to 25% by volume of water.

21. The process as defined by claim 20, the reaction being carried out in liquid phase, under a total pressure of from 50 to 1,000 bars, and at a temperature greater than about 120° C.

22. The process as defined by claim 21, the reaction being carried out at a temperature ranging from 160° to 250° C.

23. The process as defined by claim 21, the reaction being carried out under a total pressure ranging from 80 to 350 bars.

24. The process as defined by claim 1, the initial reaction medium comprising a carboxylic acid having the formula R'''-COOH, in which R''' is defined as was R, and further wherein R''' and R may be the same or different.

* * * * *